United States Patent
Francisco et al.

(10) Patent No.: US 7,892,167 B2
(45) Date of Patent: Feb. 22, 2011

(54) ENDOSCOPY SYSTEM AND A PRESSURE TRANSMITTING CONNECTOR FOR SAID SYSTEM

(75) Inventors: Andre Francisco, Sophia Antipolis (FR); Patrick Janin, Nice (FR); Thierry Pascual, Cagnes-sur-Mer (FR); Armando Dias, Saint Laurent du Var (FR)

(73) Assignee: Future Medical System S.A., Meyrin (CH)

( * ) Notice: Subject to any disclaimer, the term of this patent is extended or adjusted under 35 U.S.C. 154(b) by 852 days.

(21) Appl. No.: 10/591,441

(22) PCT Filed: Mar. 2, 2005

(86) PCT No.: PCT/CH2005/000122

§ 371 (c)(1),
(2), (4) Date: Dec. 21, 2006

(87) PCT Pub. No.: WO2005/084523

PCT Pub. Date: Sep. 15, 2005

(65) Prior Publication Data

US 2007/0185452 A1    Aug. 9, 2007

(30) Foreign Application Priority Data

Mar. 4, 2004    (FR)    .................... 04 02238

(51) Int. Cl.
*A61B 1/12*    (2006.01)
(52) U.S. Cl. .............. 600/156; 600/117; 600/130; 600/158; 600/159; 600/561; 604/65; 604/66; 604/67; 73/715; 73/716
(58) Field of Classification Search ............ 600/105, 600/117, 130, 153–159, 561; 604/65–67
See application file for complete search history.

(56) References Cited

U.S. PATENT DOCUMENTS

| 4,086,815 A | 5/1978 | Asano et al. |
| 4,132,227 A | 1/1979 | Ibe |
| 4,971,034 A * | 11/1990 | Doi et al. ............... 600/104 |
| 5,037,386 A | 8/1991 | Marcus et al. |
| 5,044,203 A | 9/1991 | Wiest et al. |
| 5,097,712 A | 3/1992 | Gerst et al. |

(Continued)

OTHER PUBLICATIONS

International Search Report mailed Jun. 2, 2005 of International Application PCT/CH2005/000122.

*Primary Examiner*—Matthew J Kasztejna
(74) *Attorney, Agent, or Firm*—Westerman, Hattori, Daniels & Adrian, LLP

(57) ABSTRACT

The inventive endoscopy system includes a cannula for arranging an endoscope and forming, between said cannula and endoscope, an irrigation or aspiration channel for transporting an irrigation or aspiration fluid, respectively, a connection ring mounted around the cannula and provided with a connection channel connectable to the irrigation or aspiration channel, respectively and a connector which is mounted on the connection ring and includes a transport channel with the connection channel and a first pressure sensor for detecting pressure in the transport channel. The connection ring is provided with a bypass circuit connectable to the irrigation or aspiration channel, respectively and the connector including a dead channel connectable to the bypass circuit and a second pressure sensor for detecting pressure in the dead channel.

7 Claims, 6 Drawing Sheets

U.S. PATENT DOCUMENTS

| | | | |
|---|---|---|---|
| 5,191,878 A * | 3/1993 | Iida et al. ................... | 600/157 |
| 5,402,770 A * | 4/1995 | Iida et al. ................... | 600/159 |
| 5,643,203 A | 7/1997 | Woolfson et al. | |
| 5,796,007 A * | 8/1998 | Panagotopulos et al. ...... | 73/716 |
| 5,810,770 A | 9/1998 | Nguyen et al. | |
| 5,836,909 A * | 11/1998 | Cosmescu ................... | 604/35 |
| 6,086,542 A | 7/2000 | Glowa et al. | |
| 7,526,960 B2 | 5/2009 | Francisco et al. | |
| 2005/0085695 A1 * | 4/2005 | Shener et al. ............... | 600/156 |

\* cited by examiner

ENDOSCOPY SYSTEM AND A PRESSURE TRANSMITTING CONNECTOR FOR SAID SYSTEM

TECHNICAL FIELD

The invention relates to an endoscopy system comprising more particularly a cannula for housing an endoscope and for forming, between the cannula and the endoscope, an irrigation channel or an outflow channel, and including a coupling ring mounted around the cannula and provided with a coupling path for communicating with the irrigation or outflow channel.

PRIOR ART

Such an endoscopy system is described for example by the documents U.S. Pat. No. 5,037,386 and U.S. Pat. No. 6,086,542. It is used in joint arthroscopy, and more particularly in knee arthroscopy. The endoscope is connected to a video screen for displaying the joint. The irrigation or outflow channel makes it possible to create a circulation of physiological saline for keeping the medium in front of the endoscope optically clear and for bathing the joint. The circulation is provided by a pump connected to a reservoir and outputting into a tubing connected to the irrigation channel or to the outflow channel via the coupling ring.

The pressure of the physiological saline in the joint is monitored by a membrane pressure sensor placed in the tubing of the irrigation channel or the outflow channel, or on a tubing connected via the coupling ring to a channel formed in the cannula and dedicated to pressure sensing, as in the case of the endoscopy systems described by the abovementioned documents. These arrangements have the drawback of resulting in the pressure being erroneously determined under certain operating conditions, for example should by accident there be a sharp bend between the pressure sensor and the coupling ring.

Document U.S. Pat. No. 5,643,203 discloses an endoscopy system of the type mentioned above, in which a connector is mounted on the coupling ring and includes a communication path for communicating with the irrigation channel and a pressure sensor for sensing the pressure in the communication path. The pressure of the physiological saline in the joint is extrapolated from a law, on the basis of the pressure sensed in the communication path.

The extrapolation of the pressure in the joint from the pressure sensed in the communication path of the connector makes it possible to dispense with a dedicated pressure-sensing channel in the cannula. Thus, it is possible for the diameter of the cannula to be decreased, for the purpose of reducing the trauma when it is being introduced into the joint. Compared to a tubing, the connector thus eliminates the risk of a variation in cross section of the communication path and allows reliable sensing of the pressure in this communication path.

However, the sensed pressure remains subject to an artificially high pressure drop in the coupling path for coupling the communication path of the connector to the irrigation channel of the cannula. This may be due to a foreign body present in the coupling path of the coupling ring and partially obstructing the flow of physiological saline in the irrigation channel.

One of the objects of the invention is to elevate this drawback so as to confer a high degree of safety on the endoscopy system.

DISCLOSURE OF THE INVENTION

For this purpose, the subject of the invention is an endoscopy system comprising a cannula for housing an endoscope and for forming, between the cannula and the endoscope, an irrigation channel and outflow channel respectively, intended for transporting an irrigation fluid and outflow fluid respectively, a coupling ring mounted around the cannula and provided with a coupling path for coupling to the irrigation channel, and to the outflow channel respectively, and a connector mounted on the coupling ring and comprising a communication path for communicating with the coupling path and a first pressure sensor for sensing the pressure in the communication path, characterized in that the coupling ring is provided with a branch-off path that communicates with the irrigation channel, and with the outflow channel respectively, and in that the connector includes a blind path communicating with the branch-off path and a second pressure sensor for sensing the pressure in this blind path.

The branch-off path of the coupling ring communicates with the blind path of the connector in order for the pressure of the fresh physiological saline flowing in the irrigation channel to be sensed a second time. The same applies when the soiled physiological saline flowing in the outflow channel is considered. Hence, it follows that the endoscopy system according to the invention has two safety levels for checking the pressure of the physiological saline in the joint.

Preferably, the branch-off path is placed downstream of the coupling path for coupling to the irrigation channel relative to the transport of the irrigating fluid and upstream of the coupling path for coupling to the outflow channel, respectively, relative to the transport of the outflow fluid, and in that an irrigation tap is provided for closing or opening the coupling path to the irrigation channel, upstream of the branch-off path, and an outflow tap is provided for closing or opening the coupling path to the outflow channel, respectively, downstream of the branch-off path. Advantageously, this arrangement makes it possible for the pressure in the joint to be always checked, even when the flow of the fresh physiological saline in the irrigation channel is interrupted by closing the irrigation tap. The same applies when the soiled physiological saline flowing in the outflow channel is considered.

The invention extends to a connector intended for an endoscopy system comprising a communication path and a pressure sensor for sensing the pressure in this communication path, characterized in that it includes a blind path and a second pressure sensor for sensing the pressure in the blind path.

Advantageously, the connector includes a second communication path. Preferably, the branch-off path is placed between the two communication paths. This arrangement makes it possible to connect the coupling ring to the communication path for irrigation, to the blind path and to the communication path for the outflow in a single operation, while still allowing pressure sensing in the blind path and one or other of the communication paths.

BRIEF DESCRIPTION OF THE DRAWINGS

Other advantages of the invention will become apparent on the reading the description of one embodiment illustrated below by the drawings.

EMBODIMENTS OF THE INVENTION

Figure 1:
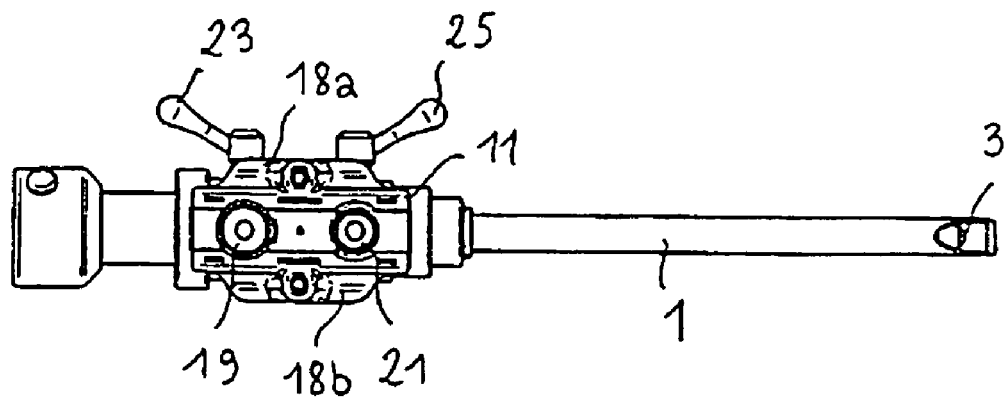
FIG. 1 shows an endoscopy system in front view.
Figure 2:
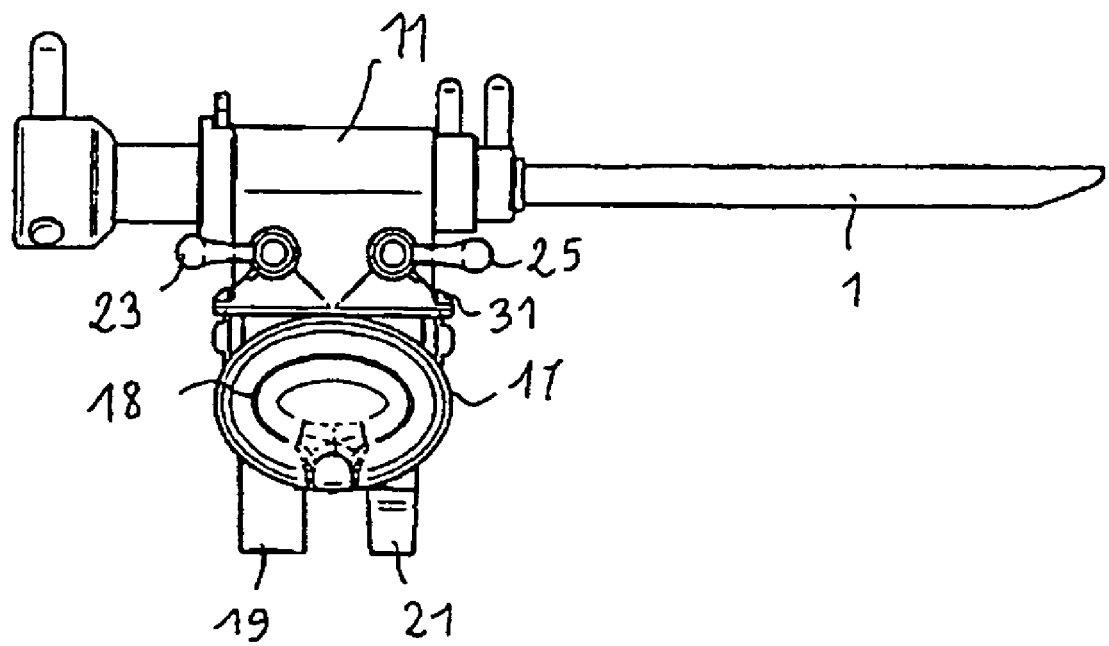
FIG. 2 shows the endoscopy system of FIG. 1 in top view.
Figure 3:
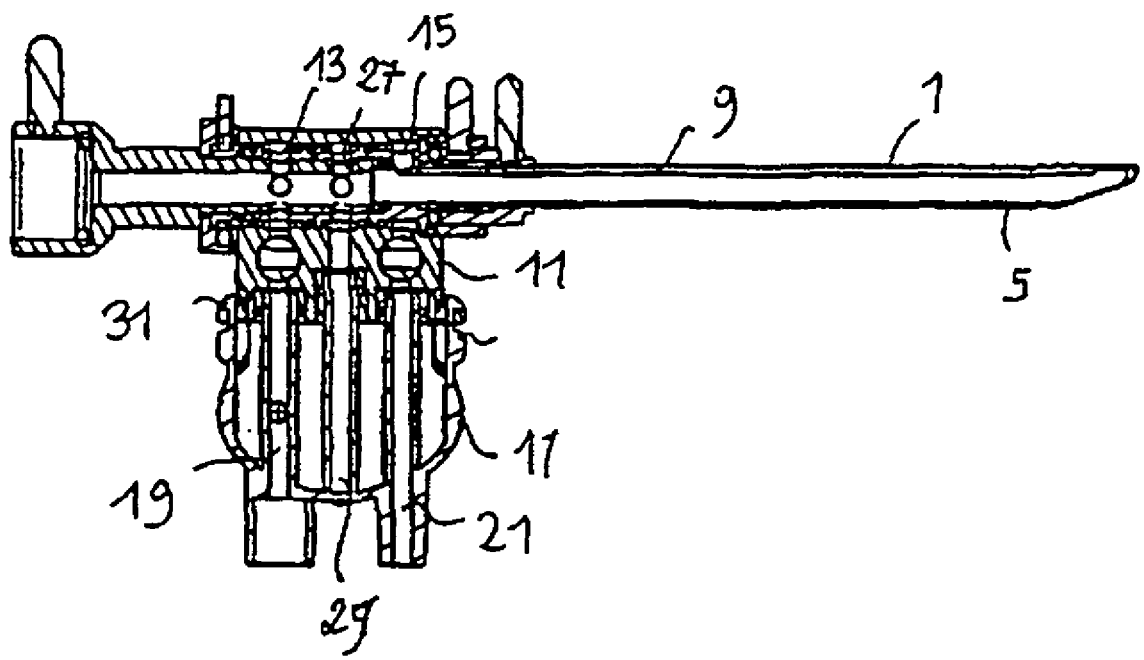
FIG. 3 shows the endoscopy system of FIG. 1 in longitudinal section.
Figure 4:
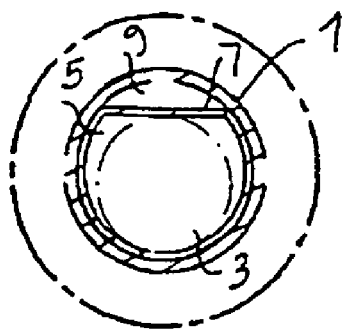
FIG. 4 shows the endoscopy system of FIG. 1 in cross section.

An endoscopy system comprises (FIGS. 1 to 4) a cannula 1 for housing an endoscope 3 and for forming, between the cannula 1 and the endoscope 3, an irrigation channel 5. In the embodiment chosen to illustrate the invention, the irrigation channel 5 is formed between the endoscope 3 and a tube 7 internal to the cannula 1, and an outflow channel 9 is formed between the internal tube 7 and the cannula 1. However, the invention also applies to a cannula having only the irrigation channel or only the outflow channel.

A coupling ring 11 is mounted around the cannula 1 in order to communicate with the irrigation channel 5 and the outflow channel 9. A first coupling path 13 communicates with the irrigation channel 5. A second coupling path 15 communicates with the outflow channel 9.

A connector 17 is mounted on the coupling ring 11. It comprises a first communication path 19, for communicating with the first coupling path 13 for coupling to the irrigation channel 5 and a first sensor 18a, and comprises a second communication path 21 for communicating with the second coupling path 15 for coupling to the outflow channel 9. The two communication paths 19 and 21 of the connector 17 are placed facing the first pressure sensor 18a for sensing the pressure in one or other (19 or 21) of these two communication paths.

Tubings (not shown) are connected to the communication paths 19 and 21 of the connector 17 and are connected to a pump in order to create a flow of fresh physiological saline in the irrigation channel 5 and of soiled physiological saline in the outflow channel 9. The coupling ring 11 includes, in a manner known per se, taps 23 and 25 for opening or closing the coupling paths 13 and 15 according to the desired flow in the irrigation channel 5 or in the outflow channel 9.

The connector 17 is mounted on the coupling ring 11 in order to allow the irrigation channel 5 and the outflow channel 9 to communicate with the two communication paths 13 and 15 of the connector without the intermediary of a tubing. With this arrangement, the pressure sensed in one or other of the communication paths of the connector is not subject to an error due to an accidental variation in the cross section of the tubings that would be connected to the coupling paths of the coupling ring.

According to the invention, the coupling ring 11 includes a branch-off path 27 for communicating with the coupling path 13 for coupling to the irrigation channel 5, whereas the connector 17 includes a blind path 29 for communicating with the branch-off path 27 and the second pressure sensor 18b for sensing the pressure in this blind path. As indicated above, the branch-off path 27 of the coupling ring communicates with the blind path 29 of the connector in order to allow the pressure of the fresh physiological saline flowing in the irrigation channel to be detected a second time.

Preferably, the branch-off path 27 is placed, relative to the transport of the irrigated fluid, downstream of the coupling path 13 for coupling to the irrigation channel 5, and the irrigation tap 23 is designed to close or open this coupling path 13 upstream of the branch-off path 27. Likewise, the branch-off path 27 is placed, relative to the transport of the outflow fluid, upstream of the coupling path 15 for coupling to the outflow channel 9, and the outflow tap 25 is designed to close or open this coupling path 15 downstream of the branch-off path 27. This arrangement makes it possible advantageously to detect the pressure in one channel—the branch-off path—undisturbed at the opening or closing, even if partial, of the tap 23 of the coupling path 13 for coupling to the irrigation channel 5, or of the tap 25 of the coupling path 15 for coupling to the outflow channel 9. In addition, the pressure in the joint may be extrapolated by means of the branch-off path, even when the flow of physiological saline is interrupted in the irrigation channel, or the outflow channel respectively, by closing the irrigation tap 23, or the outflow tap 25, respectively.

The second pressure sensing via the blind path allows the integrity of the endoscopy system according to the invention to be better checked compared with the pressures sensed by the two detectors with expected values. Thus, it is possible to diagnose a fault in the irrigation tap 23, by an abnormal pressure drop between the pressure sensed by the first detector 18a in the communication path 19 for communicating with the irrigation channel 5 and the pressure sensed by the second detector 18b in the blind path. The same applies for a fault in the outflow tap 25. These checks will advantageously be carried out by the surgeon at the start of using the endoscopy system.

INDUSTRIAL APPLICATION

Figure 5:
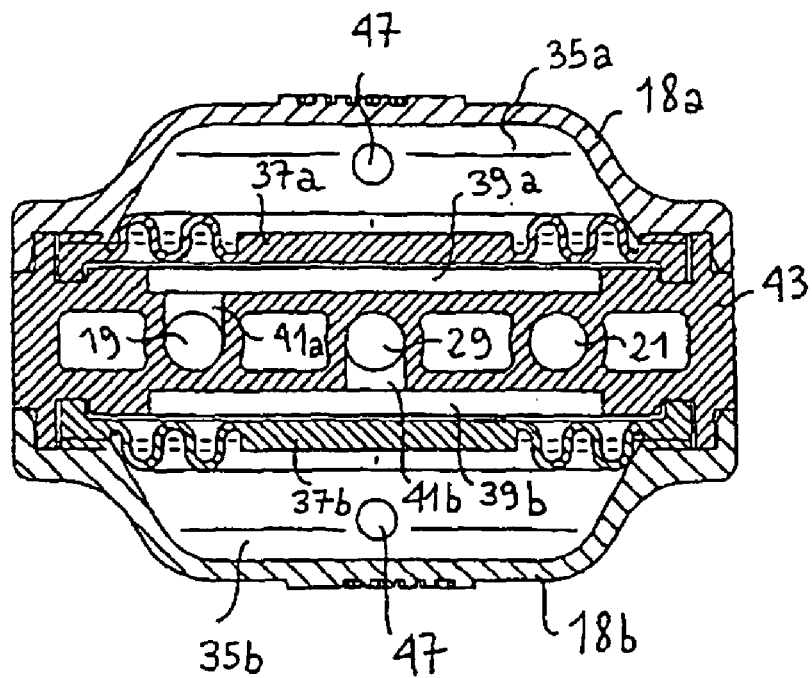
FIG. 5 shows, in cross section, a first connector intended for an endoscopy system according to the invention.
Figure 6:
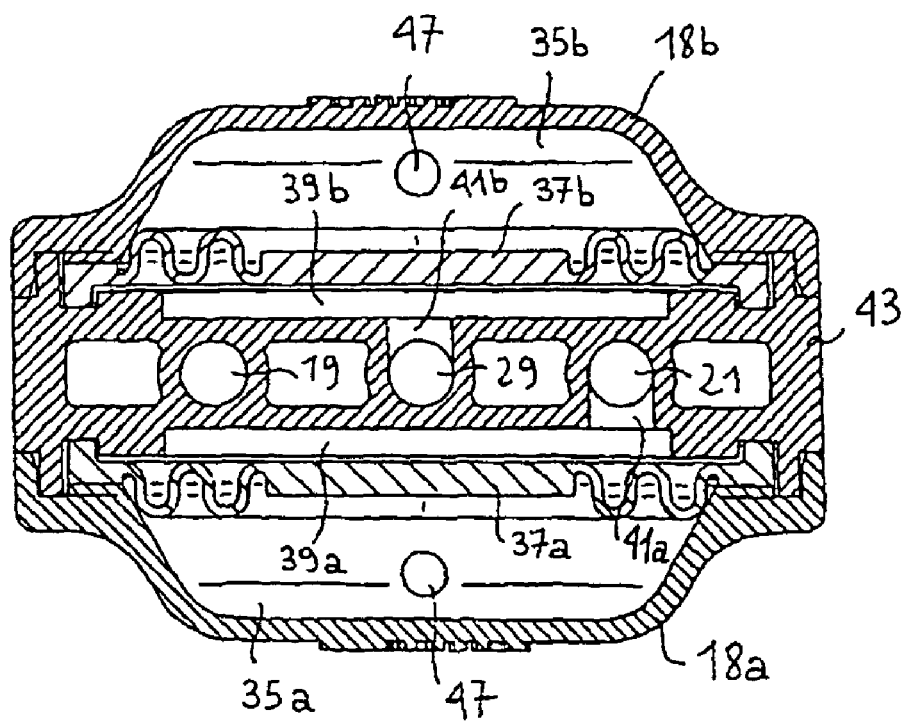
FIG. 6 shows, in cross section, a second connector intended for an endoscopy system according to the invention.

The connector of the endoscopy system according to the invention is preferably a rigid part made of an injection molded plastic and incorporates two membrane pressure sensors 18a and 18b. As may be seen in FIGS. 5 and 6, the first sensor 18a and the second sensor 18b each comprise a chamber 35a, 35b and a membrane 37a, 37b designed to be deformed and to cause the air pressure in the chamber 35a, 35b to vary. In more detail, the communication path 19, 21, the duct 41a, 41b and the fluid compartment 39a, 39b are formed in one and the same rigid part 43 to which the membrane 37a, 37b and the transmission chamber are connected in order to close off the transmission chamber on the fluid compartment 39a, 39b via the membrane 37a, 37b. The rigid part 43 is provided with means 31 for fastening it to the coupling ring 11. Preferably, the rigid part 43 is provided with a polarizing feature, for polarizing the connection on the coupling ring 11. These arrangements allow a surgeon to connect the connector to the coupling ring in an easy and reliable manner.

The physiological saline flowing in the communication path 19 for communicating with the irrigation channel 5 (FIG. 5) or in the communication path 21 for communicating with the outflow channel 9 (FIG. 6) enters the fluid compartment 39a of the first pressure sensor 18a, which is open to the communication path 13, 15 via the duct 41a and closed by the membrane 37a. This membrane 37a deforms according to the pressure of the physiological saline in the communication path 19 or 21.

Likewise, the physiological saline flowing in the irrigation channel 5 and the outflow channel 9, respectively, enters, via the branch-off path 27 and the blind path 29, into the fluid compartment 39b of the second detector 18b, which is open to the blind path 29 via the duct 41b and closed by the membrane 37b. The latter deforms according to the pressure of the physiological saline in the blind path 29.

Capillaries (not shown) are connected to connection points 47 on the transmission chambers 35a, 35b in order to transmit the variations in the air pressure inside the chambers 35a, 35b to sensors (not shown) and for determining the pressure of the physiological saline in the communication path 19, 21 and in the blind path 29.

The endoscopy system according to the invention is particularly useful in the arthroscopy of joints, such as the knee or the shoulder. As indicated above, the invention applies to a cannula that does not have a channel dedicated to sensing the pressure in the joint, so as advantageously to decrease the outside diameter of the cannula, in order to make it less traumatic when being inserted by the surgeon. However, the invention also applies to an endoscopy system in which the cannula does include a channel dedicated to measuring the pressure. The coupling ring is therefore modified so that the branch-off path communicates with the pressure dedicated channel and the connector is mounted on the coupling ring in order to bring the blind path into communication with the branch-off path.

The invention claimed is:

1. An endoscopy system comprising:
   a cannula housing an endoscope,
   an irrigation channel and an outflow channel formed respectively between the cannula and the endoscope, said irrigation channel and outflow channels being intended for transporting an irrigation fluid and outflow fluid, respectively,
   a coupling ring mounted around the cannula and provided with an irrigation coupling path in fluid communication with the irrigation channel and an outflow coupling path in fluid communication with the outflow channel, respectively,
   a connector mounted on the coupling ring and comprising an irrigation communication path in fluid communication with the irrigation coupling path and an outflow communication path in fluid communication with the outflow coupling path, respectively,
   wherein the connector comprises a first pressure sensor facing the irrigation communication path and the outflow communication path, respectively, for sensing the pressure in the irrigation and outflow communication paths, respectively, and
   wherein the coupling ring comprises a branch-off path in fluid communication with the irrigation channel and with the outflow channel, respectively,
   wherein the connector comprises a blind path in fluid communication with the branch-off path,
   and wherein the connector comprises a second pressure sensor facing the blind path for sensing the pressure in this blind path.

2. The endoscopy system as claimed in claim 1, wherein:
   the branch-off path is coupled to the irrigation channel downstream of the irrigation coupling path relative to the transport of the irrigating fluid,
   the branch-off path is coupled to the outflow channel upstream of the outflow coupling path relative to the transport of the outflow fluid, and
   an irrigation tap is provided for closing or opening the irrigation coupling path to the irrigation channel, upstream of the branch-off path, and an outflow tap is provided for closing or opening the outflow coupling path to the outflow channel, downstream of the branch-off path.

3. The system as claimed in claim 1, wherein the pressure sensors are membrane sensors.

4. The system as claimed in claim 1, wherein
   the connector comprises a rigid body provided with the irrigation and outflow communications paths and with the blind path,
   the first sensor comprises a first deformation chamber and a first membrane and the second sensor comprises a second deformation chamber and a second membrane, each of the first and second membranes being designed to be deformed and to cause pressure in the first and second chamber, respectively, to vary,
   the rigid body comprises a first transmission chamber in fluid communication with the irrigation and outflow communication paths and a second transmission chamber in fluid communication with the blind path,
   the first transmission chamber is closed off by the first membrane and the second transmission chamber is closed off by the second membrane.

5. The system as claimed in claim 4, wherein the irrigation and outflow communication paths and the blind path are located between the first and second sensors.

6. The system as claimed in claim 4, wherein the irrigation and outflow communication paths and the blind path are arranged substantially along a same plane, and the first and second sensors are arranged on opposite sides of the plane.

7. The system as claimed in claim 4, wherein the connector comprises a polarizing feature and the coupling ring comprises a corresponding polarizing feature, so that a connection of the connector on the coupling ring is polarized.

* * * * *